United States Patent
Narimatsu (10) Patent No.: US 6,612,993 B2
(45) Date of Patent: Sep. 2, 2003

(54) ARTERIOSCLEROSIS EVALUATING APPARATUS

(75) Inventor: Kiyoyuki Narimatsu, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 10/076,502

(22) Filed: Feb. 19, 2002

(65) Prior Publication Data

US 2003/0004422 A1 Jan. 2, 2003

(30) Foreign Application Priority Data

Jul. 2, 2001 (JP) .......................... 2001-200504
Dec. 13, 2001 (JP) .......................... 2001-379525

(51) Int. Cl.$^7$ ............................................. A61B 5/00
(52) U.S. Cl. ................................... 600/500; 600/485
(58) Field of Search ............................... 600/485, 490, 600/493–6, 500

(56) References Cited

U.S. PATENT DOCUMENTS

| | | | |
|---|---|---|---|
| 5,265,011 A | | 11/1993 | O'Rourke |
| 5,743,856 A | | 4/1998 | Oka et al. |
| 5,921,936 A | * | 7/1999 | Inukai et al. ............... 600/490 |
| 6,355,000 B1 | * | 3/2002 | Ogura ........................ 600/500 |

FOREIGN PATENT DOCUMENTS

EP   1 050 267 A1   11/2000
JP   9-122091 A     5/1997

* cited by examiner

Primary Examiner—Robert L. Nasser
(74) Attorney, Agent, or Firm—Oliff & Berridge, PLC (57) ABSTRACT

An apparatus for evaluating a degree of arteriosclerosis of a living subject, including a pulse-wave-propagation-velocity-related-information obtaining device which obtains pulse-wave-propagation-velocity-related information that is related to a velocity at which a pulse wave propagates in the subject, a pulse-wave sensor which is adapted to be worn on a body portion of the subject and detects the pulse wave from the body portion, an augmentation-related-information obtaining device for obtaining augmentation-related information that is related to an augmentation of an amplitude of the pulse wave detected by the pulse-wave sensor from an amplitude of an incident-wave component which is contained in the pulse wave, and an arteriosclerosis evaluating device for evaluating the degree of arteriosclerosis of the subject, based on the pulse-wave-propagation-velocity-related information obtained by the pulse-wave-propagation-velocity-related-information obtaining device and the augmentation-related information obtained by the augmentation-related-information obtaining device, according to a prescribed relationship between (A) (a1) pulse-wave-propagation-velocity-related information and (a2) augmentation-related information and (B) degree of arteriosclerosis.

13 Claims, 10 Drawing Sheets

NUMBER 1

NUMBER 2

NUMBER 3

NUMBER 4

ARTERIOSCLEROSIS EVALUATING APPARATUS

BACKGROUND OF THE INVENTION

1. Field of the Invention

The present invention relates to an arteriosclerosis evaluating apparatus for evaluating a degree of arteriosclerosis of a living subject, based on pulse-wave-propagation-velocity-related information (e.g., a pulse-wave propagation time or a pulse-wave propagation velocity) that is related to a velocity at which a pulse wave propagates in the subject.

2. Related Art Statement

Arteriosclerosis is known as a factor that influences pulse-wave-propagation-velocity-related information. This is utilized to evaluate a degree of arteriosclerosis of a living subject based on pulse-wave-propagation-velocity-related information obtained from the subject. For example, an apparatus disclosed in Japanese patent document No. 9-122091 or its corresponding U.S. Pat. No. 5,743,856 includes an electrocardiograph for detecting an electrocardiographic waveform (electrocardiogram), a pressure sensor for detecting a brachial pulse wave occurring to an inflatable cuff, and calculates, as a pulse-wave propagation time, a time difference between a time of detection of an R-wave of the electrocardiogram and a time of detection of a peak of the brachial pulse wave. In addition, the disclosed apparatus calculates a pulse wave propagation velocity by dividing, by the thus calculated pulse wave propagation time, a distance between the heart of the subject and an upper arm on which the cuff is worn.

Based on whether the thus obtained pulse-wave-propagation-velocity-related information is abnormal, it is judged whether a medical treatment, such as administration of drug, is needed.

However, if the obtained pulse-wave-propagation-velocity-related information is a value in the vicinity of a boundary between a normal range and an abnormal range, a correct judgment may not be made to administer drug, based on the pulse-wave-propagation-velocity-related information only.

Recently, it has been elucidated that there are cases where patients suffer arteriosclerosis though their pulse-wave-propagation-velocity-related information is normal and there are cases where subjects do not suffer arteriosclerosis though their pulse-wave-propagation-velocity-related information is abnormal. More specifically described, pulse-wave-propagation-velocity-related information changes with not only arteriosclerosis degree but also blood pressure. Therefore, in the case where subject's blood pressure is lowered by use of antihypertensive drug, the subject shows normal pulse-wave-propagation-velocity-related information, even if the subject may suffer arteriosclerosis. In addition, in the case where a subject suffers hypertension, the subject shows abnormal pulse-wave-propagation-velocity-related information, even though the subject may not suffer arteriosclerosis.

Meanwhile, an augmentation index, AI, is known as an index for evaluating a degree of arteriosclerosis. Generally, this index is calculated as a percentage of an augmentation between a magnitude of a peak of a pulse wave and a magnitude of a peak of an incident-wave component contained in the pulse wave, relative to a pulse pressure of the pulse wave. However, since a correlation of the augmentation index with respect to arteriosclerosis is lower than that of the pulse-wave-propagation-velocity-related information, the reliability of a diagnosis made based on the augmentation index only is low.

SUMMARY OF THE INVENTION

It is therefore an object of the present invention to provide an arteriosclerosis evaluating apparatus for evaluating a degree of arteriosclerosis of a living subject with high accuracy.

The above object has been achieved by the present invention. According to a first aspect of the present invention, there is provided an apparatus for evaluating a degree of arteriosclerosis of a living subject, comprising a pulse-wave-propagation-velocity-related-information obtaining device which obtains pulse-wave-propagation-velocity-related information that is related to a velocity at which a pulse wave propagates in the subject; a pulse-wave sensor which is adapted to be worn on a body portion of the subject and detects the pulse wave from the body portion; an augmentation-related-information obtaining means for obtaining augmentation-related information that is related to an augmentation of an amplitude of the pulse wave detected by the pulse-wave sensor from an amplitude of an incident-wave component which is contained in the pulse wave; and an arteriosclerosis evaluating means for evaluating the degree of arteriosclerosis of the subject, based on the pulse-wave-propagation-velocity-related information obtained by the pulse-wave-propagation-velocity-related-information obtaining device and the augmentation-related information obtained by the augmentation-related-information obtaining means, according to a prescribed relationship between (A) (a1) pulse-wave-propagation-velocity-related information and (a2) augmentation-elated information and (B) degree of arteriosclerosis.

According to this invention, the arteriosclerosis evaluating means evaluates the degree of arteriosclerosis, based on two sorts of information, i.e., the pulse-wave-propagation-velocity-related information obtained by the pulse-wave-propagation-velocity-related-information obtaining device and the augmentation-related information obtained by the augmentation-related-information obtaining means. Therefore, the present apparatus enjoys improved accuracy of the arteriosclerosis evaluation.

According to a second aspect of the present invention, there is provided an apparatus for evaluation of a degree of arteriosclerosis of a living subject, comprising a pulse-wave-propagation-velocity-related-information obtaining device which obtains pulse-wave-propagation-velocity-related information that is related to a velocity at which a pulse wave propagates in the subject; a pulse-wave sensor which is adapted to be worn on a body portion of the subject and detects the pulse wave from the body portion; an augmentation-related-information obtaining means for obtaining augmentation-related information that is related to an augmentation of an amplitude of the pulse wave detected by the pulse-wave sensor from an amplitude of an incident-wave component which is contained in the pulse wave; and a simultaneously displaying device which simultaneously displays the pulse-wave-propagation-velocity-related information obtained by the pulse-wave-propagation-velocity-related-information obtaining device and the augmentation-related information obtained by the augmentation-related-information obtaining means.

According to this invention, the simultaneously displaying device simultaneously displays the pulse-wave-propagation-velocity-related information and the augmentation-related information each of which reflects a degree of arteriosclerosis. Therefore, a medical person can make, based on the pulse-wave-propagation-velocity-related information and the augmentation-related information, a more accurate diagnosis about the degree of arteriosclerosis, than a diagnosis made based on the pulse-wave-propagation-velocity-related information only. For example, in the case where the medical person cannot make a clear judgment about whether there is a need to treat a patient, e.g., administer drug, based on the pulse-wave-propagation-velocity-related information only, the person can judge that the treatment is needed, if the augmentation-related information indicates that the patient suffers arteriosclerosis.

Preferably, the augmentation-related-information obtaining device comprises augmentation-index determining means for determining, as the augmentation-related information, an augmentation index indicative of the augmentation of the amplitude of the pulse wave from the amplitude of the incident-wave component, and the simultaneously displaying device comprises a display device which displays, in a two-dimensional coordinate system defined by a first axis representative of pulse-wave-propagation-velocity-related information and a second axis representative of augmentation index, a symbol at a position having a pair of coordinates corresponding to the pulse-wave-propagation-velocity-related information obtained by the pulse-wave-propagation-velocity-related-information obtaining device and the augmentation index determined by the augmentation-index determining means. According to this feature, the medical person can easily make, based on the position of the symbol displayed in the two-dimensional coordinate system, a diagnosis about the degree of arteriosclerosis.

Preferably, the display device displays the two-dimensional coordinate system which includes an arteriosclerosis area corresponding to an arteriosclerosis range of each of the pulse-wave-propagation-velocity-related information and the augmentation index represented by the first and second axes, and al least one of an arteriosclerosis-suspect area corresponding to a normal range of the pulse-wave-propagation-velocity-related information and the arteriosclerosis range of the augmentation index and a hypertension area corresponding to the arteriosclerosis range of the pulse-wave-propagation-velocity-related information and a normal range of the augmentation index. According to this feature, if the symbol is displayed in the arteriosclerosis area, the medical person can easily evaluate the degree of arteriosclerosis. If the symbol is displayed in the arteriosclerosis-suspect area, the person can speculate that the subject is highly suspected of arteriosclerosis and the subject's blood pressure is kept low by use of antihypertensive drug; and if the symbol is displayed in the hypertension area, the person can speculate that the subject is not suspected of arteriosclerosis but the subject suffers hypertension and that the subject would probably suffer arteriosclerosis in future.

Preferably, the pulse-wave-propagation-velocity-related-information obtaining device comprises an incident-wave-peak determining means for determining a peak of the incident-wave component contained in the pulse wave detected by the pulse-wave sensor; a reflected-wave-peak determining means for determining a peak of a reflected-wave component which is contained in the pulse wave detected by the pulse-wave sensor; and an obtaining means for obtaining the pulse-wave-propagation-velocity-related information based on the peak of the incident-wave component determined by the incident-wave-peak determining means and the peak of the reflected-wave component determined by the reflected-wave-peak determining means.

According to this feature, the incident-wave-peak determining means determines the peak of the incident-wave component of the pulse wave detected by the pulse-wave sensor, the reflected-wave-peak determining means determines the peak of the reflected-wave component of the pulse wave, and the obtaining means obtains the pulse-wave-propagation-velocity-related information based, e.g., a time difference between the peak of the incident-wave component and the peak of the reflected-wave component. In the case where the augmentation index is determined based on the pulse wave detected by the pulse-wave sensor, the present apparatus can obtain both the pulse-wave-propagation-velocity-related information and the augmentation index, by employing the single pulse-wave sensor.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
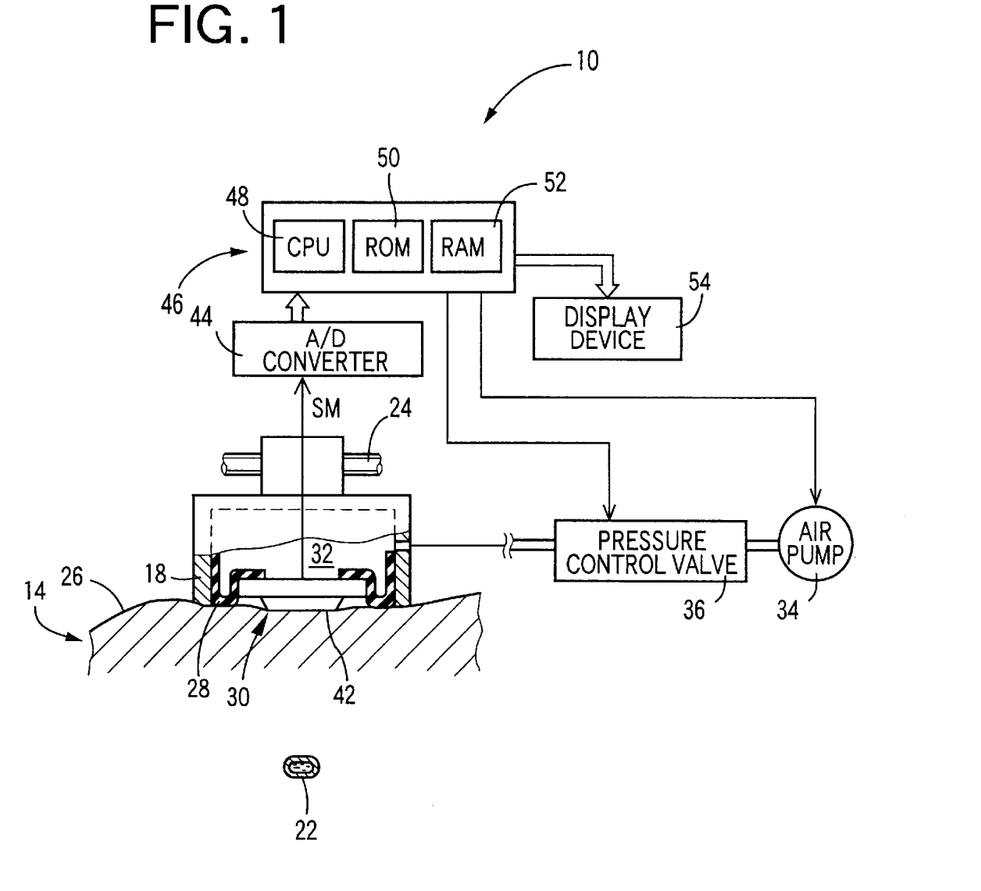
FIG. 1 is a diagrammatic view showing a circuitry of an arteriosclerosis evaluating apparatus to which the present invention is applied.

Hereinafter, there will be described an embodiment of the present invention in detail by reference to the drawings. FIG. 1 is a diagrammatic view showing a circuitry of an arteriosclerosis evaluating apparatus 10 to which the present invention is applied. The present apparatus 10 includes a pressure-pulse-wave detecting probe 12 shown in FIG. 2.

Figure 2:
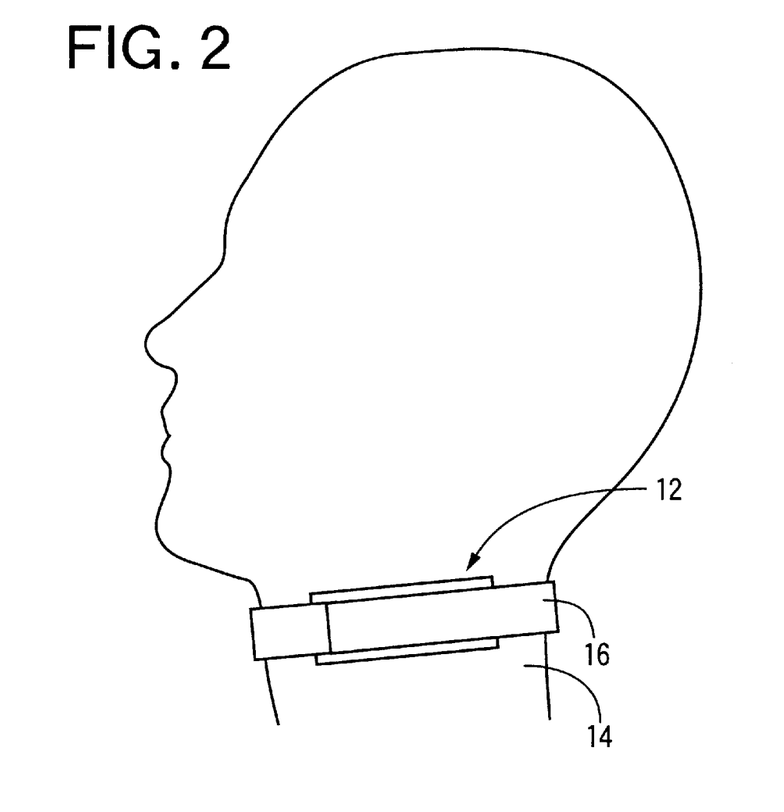
FIG. 2 is an illustrative view showing a state in which a pressure-pulse-wave detecting probe of the apparatus of FIG. 1 is worn on a neck of a living subject.

The pressure-pulse-wave detecting probe 12 is worn on a neck 14 of a living subject, as illustrated in FIG. 2, with the help of a band 16. As shown in detail in FIG. 3, the pressure-pulse-wave detecting probe 12 includes a container-like sensor housing 18; a case 20 which accommodates the sensor housing 18; and a feed screw 24 which is threadedly engaged with the sensor housing 18 and is rotated by an electric motor, not shown, provided in the case 20 so as to move the sensor housing 18 in a widthwise direction of a carotid artery 22. With the help of the band 16, the pressure-pulse-wave detecting probe 12 is detachably attached to the neck 14, such that an open end of the sensor housing 18 is opposed to a body surface 26 of the neck 14.

Figure 3:
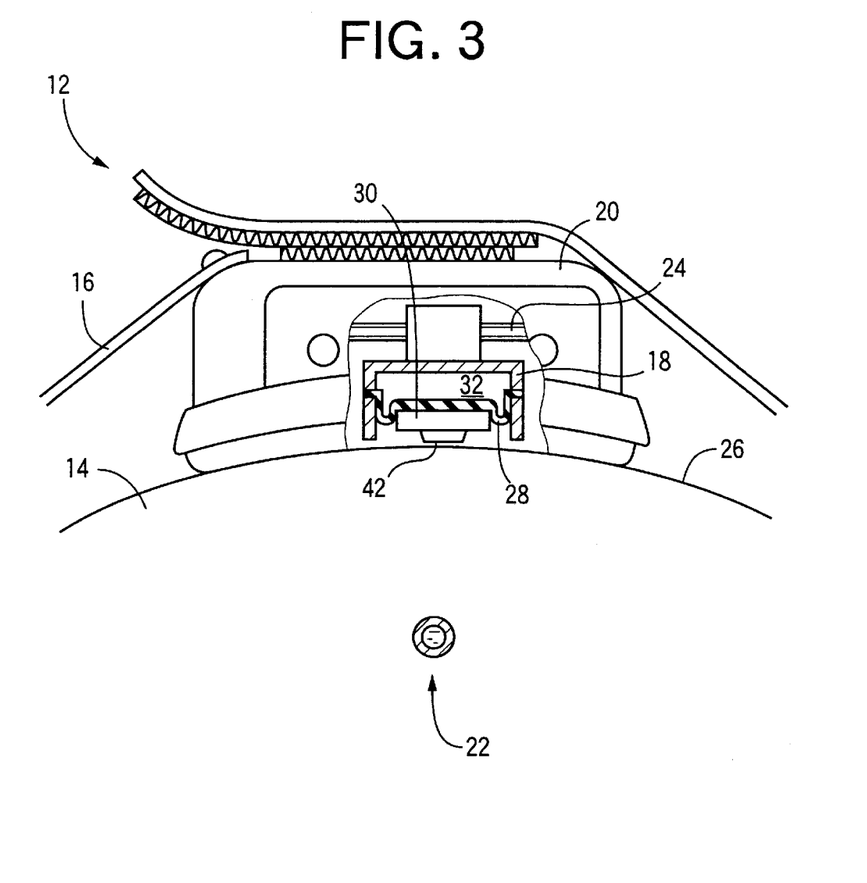
FIG. 3 is an enlarged view of the pressure-pulse-wave detecting probe of FIG. 2, a portion of the probe being cut away.

In addition, the pressure-pulse-wave detecting probe 12 includes a pressure-pulse-wave sensor 30 which is secured via a diaphragm 28 to an inner wall of the sensor housing 18, such that the sensor 30 is movable relative to the housing 18 and is advanceable out of the open end of the same 18. The sensor housing 18, the diaphragm 28, etc. cooperate with one another to define a pressure chamber 32, which is supplied with a pressurized air from an air pump 34 via a pressure-control valve 36, as shown in FIG. 1, so that the pressure-pulse-wave sensor 30 is pressed against the body surface 26 with a pressing force corresponding to the air pressure (Pa) in the pressure chamber 30. Thus, the pressing force applied to the sensor 30 is expressed in terms of the air pressure (mmHg) in the pressure chamber 32.

The sensor housing 18 and the diaphragm 28 cooperate with each other to provide a pressing device 38 which presses the pressure-pulse-wave sensor 30 against the carotid artery 22, and the feed screw 24 and the not-shown motor cooperate with each other to provide a widthwise-direction moving device 40 which moves the pressure-pulse-wave sensor 30 in the widthwise direction of the carotid artery 22 and thereby changes a pressing position where the sensor 30 is pressed on the body surface 26.

Figure 4:
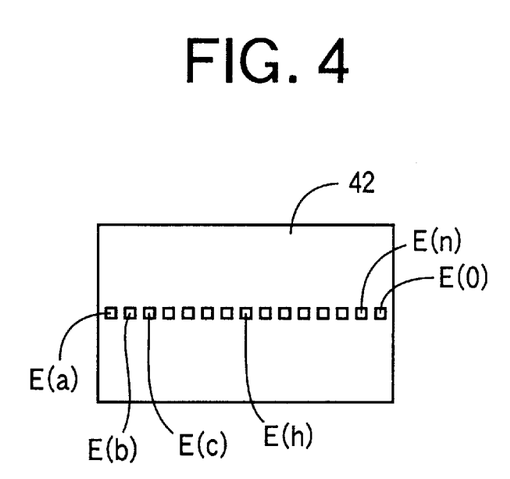
FIG. 4 is a view for explaining a state in which an array of pressure-sensing elements is provided in a press surface of a pressure-pulse-wave sensor shown in FIG. 1.

The pressure-pulse-wave sensor 30 has a pressing surface 42, and a number of semiconductor pressure-sensing elements (hereinafter, referred to as the "pressure-sensing elements") E which are arranged in the pressing surface 42 at a regular interval in the widthwise direction of the carotid artery 22, i.e., in the direction of movement of the sensor 30 parallel to the feed screw 24, over a length greater than the diameter of the carotid artery 22. For example, as shown in FIG. 4, fifteen semiconductor pressure-sensing elements E(a), E(b), ..., E(o) are arranged at a regular interval of, e.g., 0.6 mm.

Figure 5:
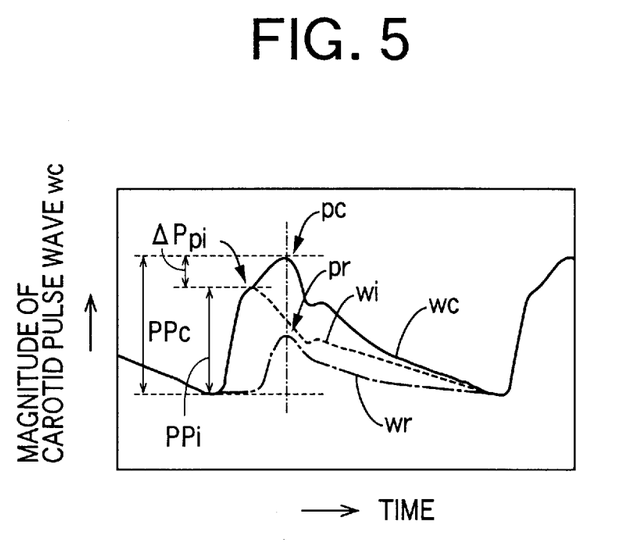
FIG. 5 is a graph showing an example of a carotid pulse wave wc represented by a pressure-pulse-wave signal SM supplied from a pressure-sensing element of the pressure-pulse-wave sensor of FIG. 1.

The pressure-pulse-wave detecting probe 12, constructed as described above, is pressed against the body surface 26 of the neck 14 right above the carotid artery 22, so that the pressure-pulse-wave sensor 30 detects a pressure pulse wave (i.e., a carotid pulse wave, wc) which is produced from the carotid artery 22 and is propagated to the body surface 26, and supplies a pressure-pulse-wave signal SM representing the detected carotid pulse wave wc, to a control device 46 via an analog-to-digital (A/D) converter 44. An example of the carotid pulse wave wc represented by the pressure-pulse-wave signal SM continuously supplied from the pressure-pulse-wave sensor 30 is indicated at solid line in FIG. 5.

The control device 46 is provided by a so-called microcomputer including a central processing unit (CPU) 48, a read only memory (ROM) 50, a random access memory (RAM) 52 and an input-and-output (I/O) port, not shown. The CPU 48 processes signals according to the control programs pre-stored in the ROM 50 by utilizing the temporary-storage function of the RAM 52. In addition, the CPU 48 supplies drive signals via the I/O port to respective drive circuits, not shown, associated with the pressure control valve 36 and the air pump 34 so as to control the pressure in the pressure chamber 32 to an optimum pressing force HDPO, described later. Moreover, the CPU 48 determines a pulse-wave propagation velocity PWV, and obtains augmentation-related information, based on the pressure-pulse-wave signal SM supplied from the pressure-pulse-wave sensor 30, and controls what is displayed by a display device 54.

Figure 6:
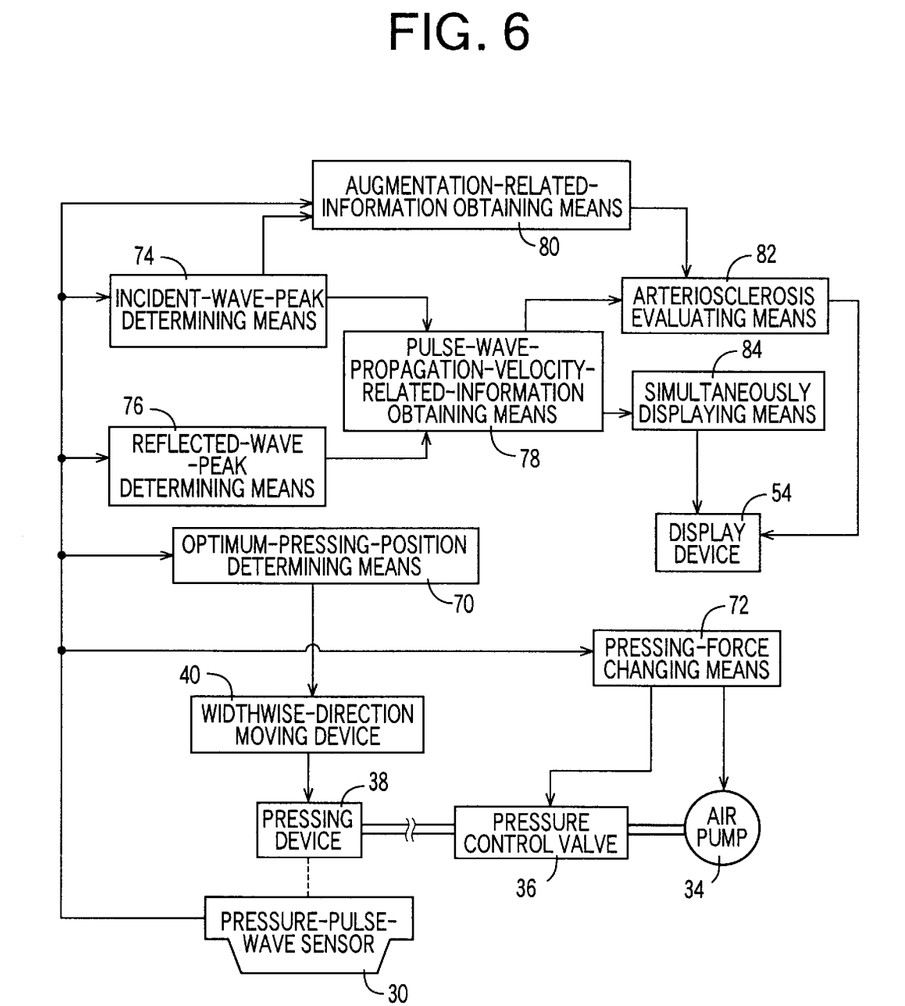
FIG. 6 is a block diagram for explaining essential control functions of a control device of the apparatus of FIG. 1.

FIG. 6 is a block diagram for explaining essential control functions of the control device 46 of the arteriosclerosis evaluating apparatus 10. An optimum-pressing-position determining means 70 judges whether a prescribed pressing-position changing condition is satisfied, i.e., whether one (hereinafter, referred to as the "highest-pressure detecting element EM") of the pressure-sensing elements E of the pressure-pulse-wave sensor 30 that detects the highest pressure of the respective pressures detected by all the elements E is positioned in one of prescribed opposite end portions of the array of pressure-sensing elements E. Each of the prescribed opposite end portions of the array of elements E may be a range having a prescribed length including a corresponding one of the opposite ends of the array of elements E, or a range accommodating a prescribed number of elements E including a corresponding one of the respective elements E located at the opposite ends of the array. The highest-pressure detecting element EM is one of the elements E that is positioned right above the carotid artery 22. When this pressing-position changing condition is satisfied, the optimum-pressing-position determining means 70 carries out the following pressing-position changing operation: After the pressing device 38 once moves the pressure-pulse-wave sensor 30 away from the body surface 26, the widthwise-direction moving device 40 moves the pressing device 38 and the sensor 30 over a prescribed distance, and then the pressing device 38 again presses the sensor 30 with a prescribed, considerably low first pressing force HDP1. In this state, the determining means 70 judges again whether the prescribed pressing-position changing condition is satisfied. The determining means 70 repeats carrying out the above-described operation and judgment till the pressing-position changing condition is not satisfied any longer, preferably till the highest-pressure detecting element EM is positioned in a prescribed middle portion of the array of elements E. The length, or element number, employed for each of the opposite end portions of the array of elements E is prescribed based on the diameter of the artery (i.e., the carotid artery 22) to be pressed by the pressure-pulse-wave sensor 30, and may be one fourth of the diameter.

A pressing-force changing means 72 changes, after the optimum-pressing-position determining means 70 positions the pressure-pulse-wave sensor 30 at the optimum pressing position, a pressing force HDP (i.e., a hold-down pressure) applied by the pressing device 38 to the sensor 30, within a prescribed pressing-force range, either stepwise in response to each heartbeat of the subject or continuously at a prescribed, considerably low rate. Based on the carotid pulse wave wc obtained during the changing of the pressing force HDP, the changing means 72 determines an optimum pressing force HDPO and maintains the pressing force applied by the pressing device 38 to the sensor 30, at the thus determined optimum pressing force HDPO. Here, the optimum pressing force HDPO is so determined that a pulse pressure PPc of the carotid pulse wave wc (i.e., a value obtained by subtracting a minimal value, from a maximal value, of one heartbeat-synchronous pulse of the carotid pulse wave wc) detected by the highest-pressure detecting element EM pressed by the pressing force HDP may not be smaller than a predetermined lower-limit pulse pressure $PPc_L$. The lower-limit pulse pressure $PPc_L$ is experimentally determined as a value which assures that a reference point used to obtain pulse-wave-propagation-velocity-related information can be accurately identified on the carotid pulse wave wc. If the pulse pressure PPc is too small, a clear carotid pulse wave wc is not obtained and accordingly accuracy of determination of the reference point on the carotid pulse wave wc is lowered.

An incident-wave-peak determining means 74 successively determines an amplitude (i.e., a pulse pressure PPi), and a time of occurrence, of a peak, pi, of an incident-wave component, wi, which is contained in each of successive heartbeat-synchronous pulses of the carotid pulse wave wc continuously detected by the highest-pressure detecting element EM of the pressure-pulse-wave sensor 30 in the state in which the pressing force HDP applied to the sensor 30 is maintained at the optimum pressing force HDPO. The carotid pulse wave wc contains the incident-wave component wi, indicated at broken line in FIG. 5, and the peak pi of the incident-wave component wi corresponds to an inflection point or a maximal point of the composite carotid pulse wave wc (i.e., observed wave) that occurs between a rising point and a peak point, pc, of the composite wave wc (in the example shown in FIG. 5, the peak pi of the incident wave wi corresponds to an inflection point of the observed wave wc). To this end, the incident-wave-peak determining means 74 subjects the continuously obtained pressure-pulse-wave signal SM to a prescribed mathematical treatment, to detect an inflection point or a maximal point occurring between a rising point and a peak point pc of each heartbeat-synchronous pulse of the carotid pulse wave wc represented by the signal SM, and determines a time of occurrence of the inflection point or the maximal point as a time of occurrence of the peak pi of the incident wave wi. Here, the mathematical treatment may be a common treatment used to detect an inflection point or a maximal point; such as a differentiation treatment or a filter treatment.

A reflected-wave-peak determining means 76 successively determines a time of occurrence of a peak, pr, of a reflected-wave component, wr, which is contained in each of the successive heartbeat-synchronous pulses of the same carotid pulse wave wc as that on which the incident-wave-peak determining means 74 successively determines the time of occurrence of the peak pi of the incident-wave component wi. The carotid pulse wave wc contains the reflected-wave component wr, indicated at one-dot chain line in FIG. 5, and the peak pr of the reflected-wave component wr corresponds to the peak pc of the observed wave wc. To this end, the reflected-wave-peak determining means 76 detects a peak point pc of each of successive heartbeat-synchronous pulses of the carotid pulse wave wc represented by the continuously obtained pressure-pulse-wave signal SM, and determines a time of occurrence of the peak point pc as a time of occurrence of the peak pr of the reflected wave wr. It is speculated that a main component of the reflected-wave component wr is one which is produced from the heart of the subject and then reflected around an iliac artery of the subject.

A pulse-wave-propagation-velocity-related-information obtaining means 78 successively determines, as a pulse-wave propagation time DT (sec), a time difference between the time of occurrence of the peak pi of the incident-wave component wi successively determined by the incident-wave-peak determining means 74 and the time of occurrence of the peak pr of the reflected-wave component wr successively determined by the reflected-wave-peak determining means 76. Then, the obtaining means 78 successively calculates a pulse-wave propagation velocity PWV (m/sec), i.e., a velocity at which a pulse wave propagates through an artery of the subject, by substituting the thus determined propagation time DT for a parameter, DT, of the following Expression 1:

$$PWV = L/DT \qquad \text{(Expression 1)}$$

In Expression 1, symbol L (m) indicates a distance equal to twice the distance between the aortic valve of the subject and the reflection point around the iliac artery of the subject, and is experimentally determined in advance. Each of the pulse-wave propagation time DT and the pulse-wave propagation velocity PWV is obtained as a piece of pulse-wave-propagation-velocity-related information.

An augmentation-related-information obtaining means 80 obtains, based on the carotid pulse wave wc continuously detected by the highest-pressure detecting element EM of the pressure-pulse-wave sensor 30 in the state in which the pressing force HDP applied to the sensor 30 is maintained at the optimum pressing force HDPO, a piece of augmentation-related information that is related to an augmentation of an amplitude (i.e., a pulse pressure PPc) of the carotid pulse wave wc from an amplitude (i.e., a pulse pressure PPi) of the incident-wave component wi. The augmentation-related information may be an augmentation index, AI, that indicates the augmentation of the pulse pressure PPc of the carotid pulse wave wc from the pulse pressure PPi of the incident-wave component wi, or one of waveform-pattern numbers that corresponds to the difference of the pulse pressure PPc of the carotid pulse wave wc from the pulse pressure PPi of the incident-wave component wi.

The augmentation index AI may be determined as a percentage of a difference, $\Delta P$, of the pulse pressure PPc of the carotid pulse wave wc from the pulse pressure PPi of the incident-wave component wi, relative to the pulse pressure PPc, i.e., according to the following Expression 2:

$$AI = (\Delta P/PPc) \times 100 \qquad \text{(Expression 2)}$$

Otherwise, the augmentation index AI may be determined as a value ($=PPi/PPc=PPi/(PPi+\Delta P)$) obtained by dividing, by the pulse pressure PPc of the carotid pulse wave wc, the pulse pressure PPi of the incident-wave component wi; a value ($=PPc/PPi=(PPi+\Delta P)/PPi$) obtained by dividing the pulse pressure PPc of the carotid pulse wave wc, by the pulse pressure PPi of the incident-wave component wi; a value ($=\Delta P/PPi$) obtained by dividing the difference $\Delta P$ by the pulse pressure PPi of the incident-wave component wi; a value ($=PPc/\Delta P$) obtained by dividing, by the difference $\Delta P$, the pulse pressure PPc of the carotid pulse wave wc; a value ($=PPi/\Delta P$) obtained by dividing, by the difference $\Delta P$, the pulse pressure PPi of the incident-wave component wi; or a percentage of each of the above values.

Figure 7:
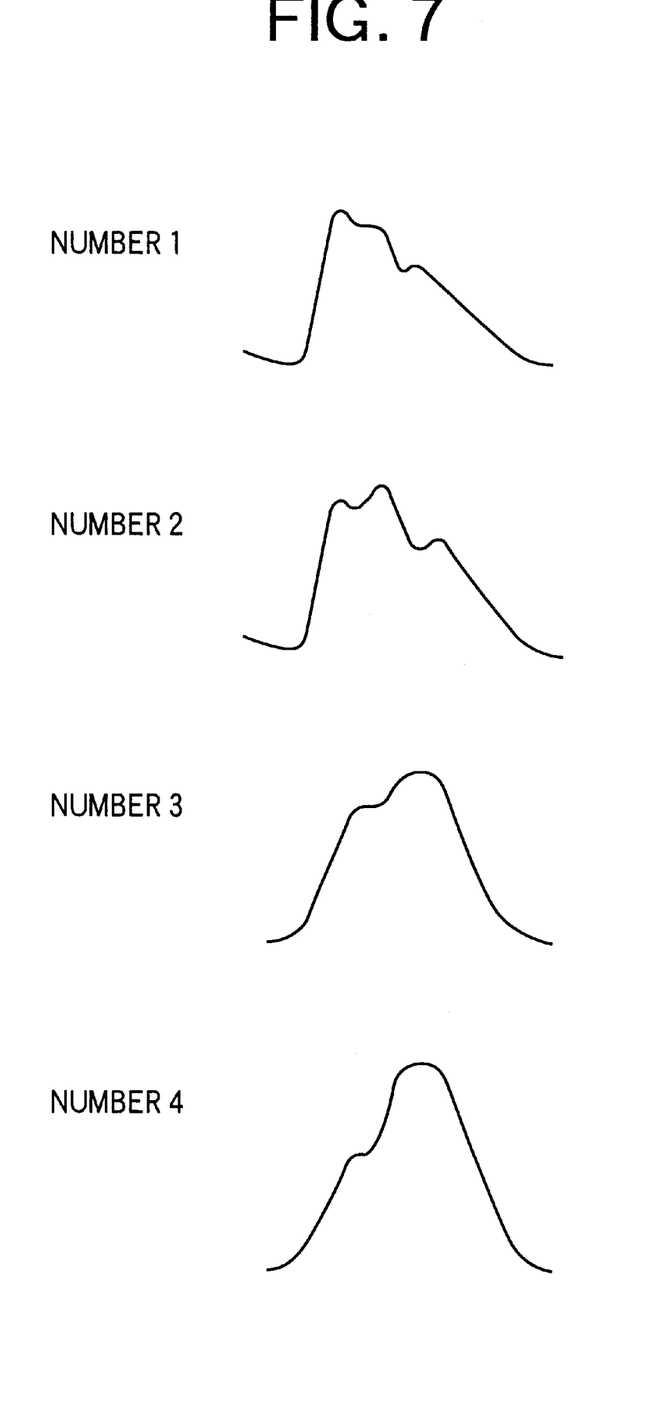
FIG. 7 is a graph showing typical waveforms corresponding to respective waveform-pattern numbers one of which is selected as augmentation-related information.

The waveform-pattern numbers may pattern numbers 1, 2, 3, and 4, shown in FIG. 7, that correspond to four different waveforms, respectively. Pattern number 1 corresponds to the lowest arteriosclerosis degree, and pattern number 4 corresponds to the highest arteriosclerosis degree. As the pattern numbers increase, the arteriosclerosis degrees increase. Pattern number 1 corresponds to a waveform in which the first maximal point occurring after a rising point of a heartbeat-synchronous pulse coincides with the greatest point of the pulse; pattern number 2 corresponds to a waveform in which a difference between a magnitude of the first maximal point or inflection point after a rising point of a pulse and a magnitude of the greatest point of the pulse is smaller than a first reference value; pattern number 3 corresponds to a waveform in which a difference between a magnitude of the first maximal point or inflection point after a rising point of a pulse and a magnitude of the greatest point of the pulse is not smaller than the first reference value and smaller than a second reference value greater than the first reference value; and pattern number 4 corresponds to a waveform in which a difference between a magnitude of the first maximal point or inflection point after a rising point of a pulse and a magnitude of the greatest point of the pulse is not smaller than the second reference value. Each waveform pattern can be classified into one of the pattern numbers 1 to 4, because, as the degree of arteriosclerosis increases, the magnitude of the reflected-wave component increases and accordingly the magnitude of the greatest point of the composite pulse wave increases relative to the magnitude of the incident-wave component (i.e., the magnitude of the first maximal or inflection point of the incident-wave component after the rising point thereof).

An arteriosclerosis evaluating means 82 evaluates a degree of arteriosclerosis of a patient, based on the pulse-wave-propagation-velocity-related information obtained by the pulse-wave-propagation-velocity-related-information obtaining means 78, and the augmentation-related information obtained by the augmentation-related-information obtaining means 80, according to a prescribed relationship between (A) (a1) pulse-wave-propagation-velocity-related information and (a2) augmentation-related information, and (B) degree of arteriosclerosis. The prescribed relationship is stored, in advance, in the ROM 50. Here, it is assumed that the ROM 50 stores a prescribed relationship between pulse wave propagation velocity PWV as (a1) pulse-wave-propagation-velocity-related information and augmentation index AI, calculated according to Expression 2, as (a2) augmentation-related information, and (B) degree of arteriosclerosis. Each of pulse wave propagation velocity PWV and augmentation index AI changes with arteriosclerosis degree. More specifically described, as arteriosclerosis degree increases, pulse wave propagation velocity PWV increases, and augmentation index AI increases. Therefore, for each of pulse wave propagation velocity PWV and augmentation index AI, a normal range and an arteriosclerosis-suspect range are experimentally determined in advance. The relationship pre-stored in the ROM 50 is so prescribed that the arteriosclerosis evaluating means 82 judges that the patient suffers arteriosclerosis, if each of the pulse wave propagation velocity PWV and the augmentation index AI obtained from the patient falls in the arteriosclerosis-suspect range, and judges that the patient is normal, if each of the pulse wave propagation velocity PWV and the augmentation index AI falls in the normal range. In addition, the above relationship is so prescribed that the arteriosclerosis evaluating means 82 judges that the patient suffers hypertension, if the pulse wave propagation velocity PWV falls in the arteriosclerosis-suspect range but the augmentation index AI falls in the normal range. In this case, it can be speculated that the patient shows the pulse wave propagation velocity PWV that does not fall in the normal range, because the patient suffers hypertension, and that the patient does not suffer arteriosclerosis. On the other hand, if the pulse wave propagation velocity PWV falls in the normal range but the augmentation index AI falls in the arteriosclerosis-suspect range, it can be speculated that the patient is suspected of arteriosclerosis and that the patent may show the pulse wave propagation velocity PWV falling in the normal range, because of use of antihypertensive drug. In this case, the arteriosclerosis evaluating means 82 judges, according to the above relationship, that the patient is suspected of arteriosclerosis and needs medical observation.

A simultaneously displaying means 84 operates the display device 54 to simultaneously display the pulse-wave-propagation-velocity-related information obtained by the pulse-wave-propagation-velocity-related-information obtaining means 78, and the augmentation-related information obtained by the augmentation-related-information obtaining means 80. For example, the displaying means 84 operates the display device 54 to display the pulse-wave-propagation-velocity-related information (value) and the augmentation index AI (value), side by side. Alternatively, the displaying means 84 operates the display device 54 to display, in a two-dimensional coordinate system defined by a first axis indicative of pulse-wave-propagation-velocity-related information and a second axis indicative of augmentation index AI, a symbol at a position having a pair of coordinates corresponding to the pulse-wave-propagation-velocity-related information and the augmentation index AI that are actually obtained from the patient.

Figure 8:
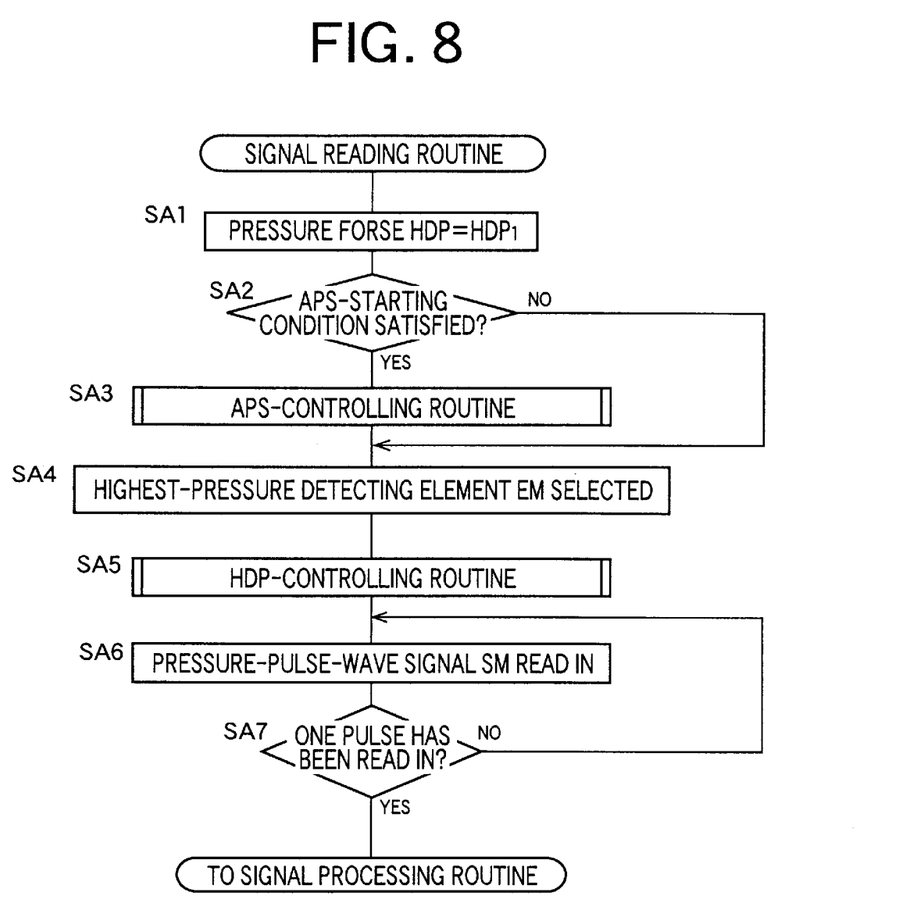
FIG. 8 is a flow chart for explaining more concretely the control functions of the control device, shown in FIG. 6, particularly, a signal reading routine.
Figure 9:
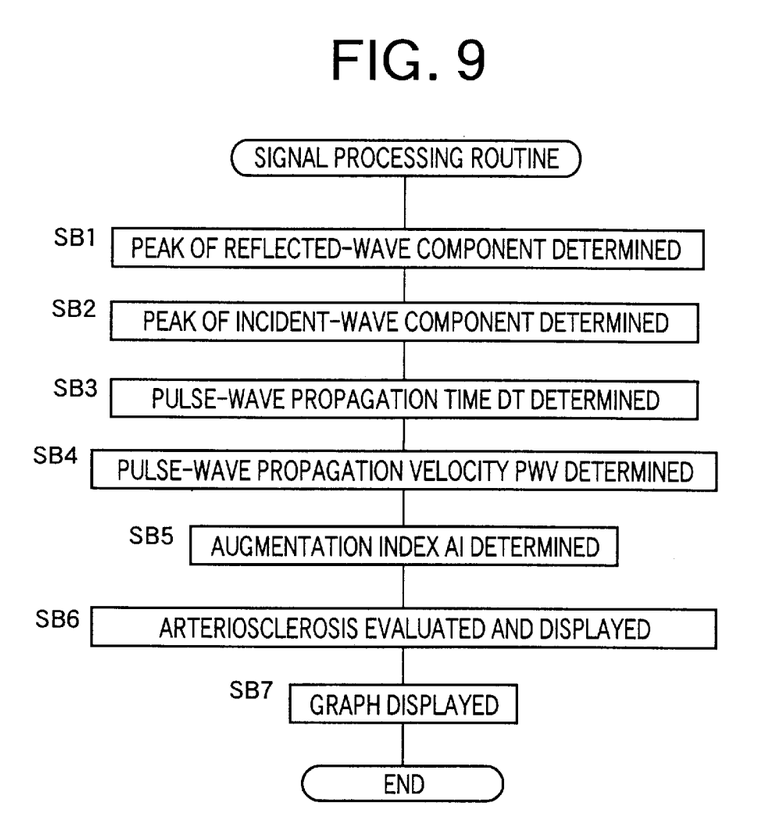
FIG. 9 is a flow chart for explaining more concretely the control functions of the control device, shown in FIG. 6, particularly, a signal processing routine.

FIGS. 8 and 9 are flow charts representing the control functions of the control device 46 shown in FIG. 6. FIG. 8 shows a signal reading routine for reading the pressure-pulse-wave signal SM; and FIG. 9 shows a signal processing routine for processing the thus read pressure-pulse-wave signal SM.

In FIG. 8, the control device 46 carries out Steps SA1 to SA3 (hereinafter, the term "Step(s)" is omitted, if appropriate) corresponding to the optimum-pressing-position determining means 70. First, at SA1, the control device operates the pressing device 38 to change the pressure in the pressure chamber 32 so that the pressing force HDP applied to the pressure-pulse-wave sensor 30 is held at the prescribed first pressing force HDP1. The first pressing force HDP1 is experimentally determined, in advance, as a pressing force HDP which assures that an S/N ratio of the carotid pulse wave wc detected by each pressure-sensing element E is high enough to allow the peak pc of the carotid pulse wave wc to be detected with considerably high accuracy.

Then, the control proceeds with SA2 where the control device judges whether the prescribed pressing-position changing condition (i.e., the APS-starting condition) is satisfied, i.e., whether the highest-pressure-detecting element EM as one of the pressure-sensing elements E provided in the pressing surface 42 is located in one of the prescribed opposite end portions of the array of elements E. If a negative judgment is made at SA2, the control goes to SA4 and the following steps, described later.

On the other hand, if a positive judgment is made at SA2, that is, if the pressing position where the pressure-pulse-wave sensor 30 is pressed against the carotid artery 22 is not appropriate, the control proceeds with SA3, i.e., an APS-controlling routine. According to this APS-controlling routine, the control device determines the optimum pressing position where the highest-pressure-detecting element EM is located at substantially the middle of the array of elements E. To this end, the control device operates the pressing device 38 and the widthwise-direction moving device 40 to once move the pressure-pulse-wave sensor 30 off the body surface 26, move the pressing device 38 and the sensor 30 over a prescribed distance, and again press the sensor 30 with the prescribed pressing force HDP1. In this state, the control device again judges whether the highest-pressure-detecting element EM is located at substantially the middle of the array of elements E. SA2 and SA3 are repeated till a positive judgment is made at SA2.

Thus, at SA3, the control device positions the pressure-pulse-wave sensor 30 at the optimum pressing position. Then, the control goes to SA4 where the control device selects, in this state, a new highest-pressure detecting element EM from the pressure-sensing elements E of the sensor 30. SA4 is followed by SA5 corresponding to the pressing-force changing means 72, where the control device carries out the HDP-controlling routine in which the pressing force HDP applied by the pressing device 38 to the sensor 30 is continuously increased from the first pressing force HDP1. During this increasing of the pressing force HDP, the control device determines an optimum pressing force HDPO based on a judgment about whether a pulse pressure PPc of each of successive heartbeat-synchronous pulses of the carotid pulse wave wc detected by the highest-pressure detecting element EM selected at SA4 is not smaller than the prescribed lower-limit pulse pressure $PPc_L$. Then, the control device maintains the pressing force HDP applied to the pressure-pulse-wave sensor 30, at the thus determined optimum pressing force HDPO.

Then, the control goes to SA6 where the control device reads in the pressure-pulse-wave signal SM supplied from the highest-pressure detecting element EM of the pressure-pulse-wave sensor 30 and, then at SA7, the control device judges whether the control device has read in one heartbeat-synchronous pulse of the pressure-pulse-wave signal SM, e.g., by judging whether the control device has read in a rising point of a heartbeat-synchronous pulse of the carotid pulse wave that follows a rising point of its preceding heartbeat-synchronous pulse. If a negative judgment is made at SA7, SA6 and the following steps are repeated to continue reading in the pressure-pulse-wave signal SM. Meanwhile, if a positive judgment is made at SA7, then the control device carries out the signal processing routine shown in FIG. 9.

Next, the signal processing routine of FIG. 9 will be explained. First, at SB1 corresponding to the reflected-wave-peak detecting means 76, the control device determines a peak pc of the one pulse of the carotid pulse wave wc represented by the pressure-pulse-wave signal SM read in at SA6 of FIG. 8, stores a magnitude of the peak pc in the RAM 52, and determines a time of occurrence of the peak pc as a time of occurrence of a peak pr of the reflected-wave component wr of the carotid pulse wave wc. The thus determined time of occurrence of the peak pr is also stored in the RAM 52.

Then, the control goes to SB2 corresponding to the incident-wave-peak determining means 74. At SB2, the control device subjects, to a fourth-order differentiation treatment or analysis, a portion or length of the pressure-pulse-wave signal SM, read in at SA6 of FIG. 8, that continues from a time corresponding to the rising point of the carotid pulse wave wc and to the time corresponding to the peak pc determined at SB1, and thereby determines an inflection point or a maximal point occurring to the length of the signal SM. A time of occurrence of the inflection or maximal point is determined as a time of occurrence of a peak pi of the incident-wave component wi, and is stored in the RAM 52. In addition, a magnitude of the inflection or maximal point is stored, in the RAM 52, as a magnitude of the peak pi of the incident-wave component wi.

Subsequently, the control goes to SB3 and SB4 corresponding to the pulse-wave-propagation-velocity-related-information obtaining means 78. At SB3, the control device determines a pulse-wave propagation time DT by subtracting the time of occurrence of the peak pi of the incident-wave wi, determined at SB2, from the time of occurrence of the peak pr of the reflected-wave wr, determined at SB1. Subsequently, at SB4, the control device determines, according to the above-indicated Expression 1, a pulse-wave propagation velocity PWV based on the pulse-wave propagation time DT determined at SB3.

Then, the control goes to SB5 corresponding to the augmentation-related-information obtaining means 80. At SB5, the control device calculates a peak difference ΔP by subtracting the magnitude of the peak pi of the incident-wave component wi, determined at SB2, from the magnitude of the peak pc of the carotid pulse wave wc, determined at SB1. In addition, the control device calculates a pulse pressure PPc by subtracting the minimal value, from the maximal value, of the one pulse of the carotid pulse wave wc read in at SA6 of FIG. 8, and calculates an augmentation index AI (%) by substituting the thus obtained peak difference ΔP and pulse pressure PPc for the corresponding variables of the above-indicated Expression 2.

Subsequently, the control goes to SB6 corresponding to the arteriosclerosis evaluating means 82. At SB6, the control device evaluates a degree of arteriosclerosis of the subject, based on the pulse wave propagation velocity PWV determined at SB4 and the augmentation index AI determined at SB5, according to an arteriosclerosis-evaluate map 86, shown in FIG. 10, that is pre-stored in the ROM 50. In addition, the control device operates the display device 54 to display a result of the evaluation.

Figure 10:
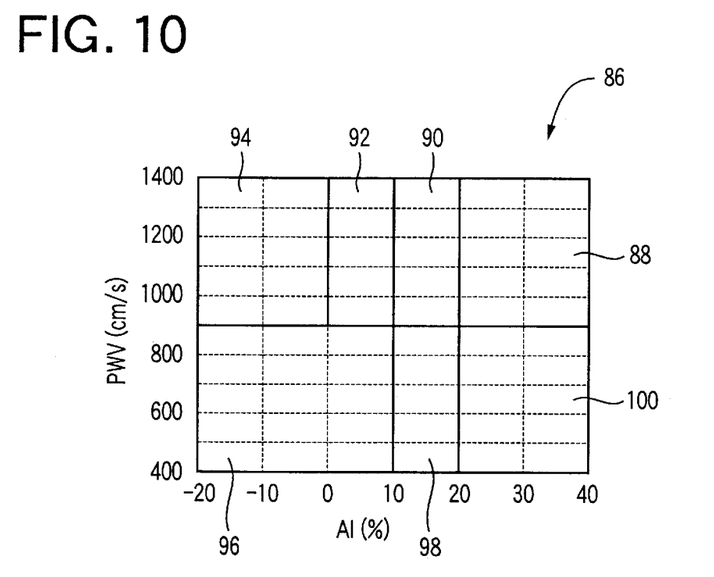
FIG. 10 is a view showing a two-dimensional coordinate system defined by a first axis indicative of pulse wave propagation velocity PWV and a second axis indicative of augmentation index AI, the coordinate system including a normal range.

Here, the arteriosclerosis-evaluate map 86 shown in FIG. 10 is described in detail. The arteriosclerosis-evaluate map 86 defines, for the pulse-wave propagation velocity PWV, a normal range not higher than 900 cm/s and an abnormal range (i.e., an arteriosclerosis-suspect range) higher than 900 cm/s, and defines, for the augmentation index AI, a normal range not higher than 10% and an abnormal range (i.e., an arteriosclerosis-suspect range) higher than 10%. The map 86 includes a first arteriosclerosis area 88 which corresponds to the above-indicated abnormal range of the pulse-wave propagation velocity PWV and a not lower than 20% portion of the above-indicated abnormal range of the augmentation index AI and which indicates that a subject suffers a high degree of arteriosclerosis; a second arteriosclerosis area 90 which corresponds to the abnormal range of the propagation velocity PWV and a 10 to 20% portion of the abnormal range of the augmentation index AI and which indicates that a subject suffers a medium degree of arteriosclerosis; a third arteriosclerosis area 92 which corresponds to the abnormal range of the propagation velocity PWV and a 0 to 10% portion of the above-indicated normal range of the augmentation index AI and which indicates that a subject suffers arteriosclerosis but its degree is low; a hypertension area 94 which corresponds to the abnormal range of the propagation velocity PWV and a not higher than 0% portion of the normal range of the augmentation index AI and which indicates that a subject suffers hypertension; a normal range 96 which corresponds to the normal range of each of the propagation velocity PWV and the augmentation index AI; and a first arteriosclerosis-suspect area 98 which corresponds to the normal range of the propagation velocity PWV and the 10 to 20% portion of the abnormal range of the augmentation index AI and which indicates that a subject cannot be diagnosed as an arteriosclerosis case but is suspected of it; and a second arteriosclerosis-suspect area 100 which corresponds to the normal range of the propagation velocity PWV and the not lower than 20% portion of the abnormal range of the augmentation index AI and which indicates that a subject cannot be diagnosed as an arteriosclerosis case but is more highly suspected of it.

Figure 11:
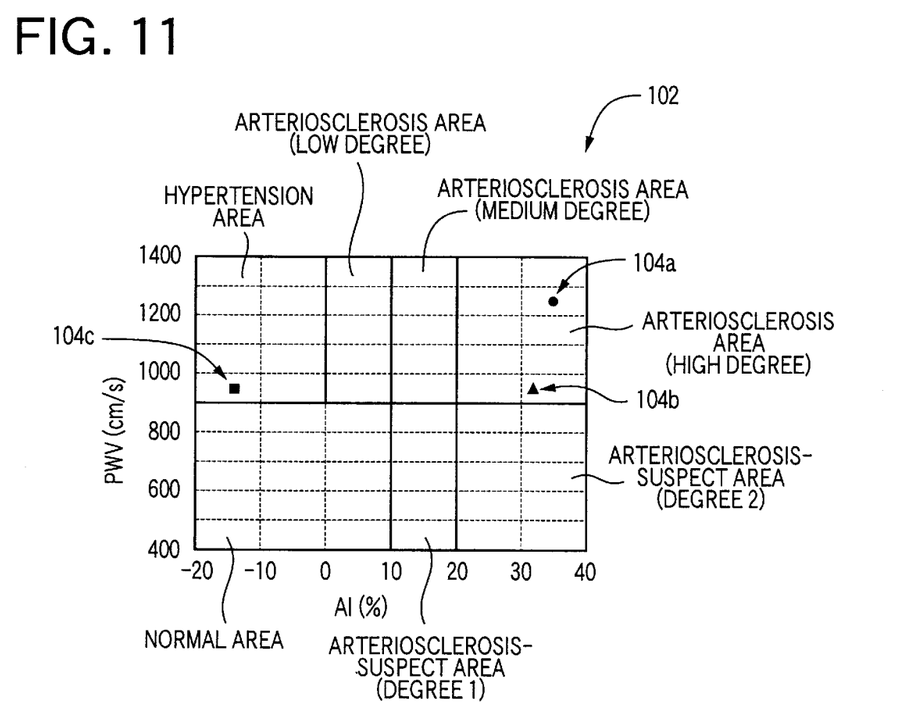
FIG. 11 is a two-dimensional coordinate system displayed on a screen of a display device at Step SB7 of FIG. 9.

Then, the control goes to SB7 corresponding to the simultaneously displaying means 84. At SB7, the control device operates the display device 54 to display, in a two-dimensional coordinate system 102 defined by a first axis representative of pulse-wave propagation velocity PWV and a second axis representative of augmentation index AI, as shown in FIG. 11, a symbol 104 at a position having a pair of coordinates corresponding to the augmentation index AI determined at SB5 and the pulse-wave propagation velocity PWV determined at SB4. As shown in FIG. 11, the display device 54 displays, in the two-dimensional coordinate system 102, respective indications corresponding to the various areas 88 to 100 shown in FIG. 10. More specifically described, the display device 54 displays the indication "ARTERIOSCLEROSIS AREA (HIGH DEGREE)" for the first arteriosclerosis area 88, the indication "ARTERIOSCLEROSIS AREA (MEDIUM DEGREE)" for the second arteriosclerosis area 90, the indication "ARTERIOSCLEROSIS AREA (LOW DEGREE)" for the third arteriosclerosis area 92, the indication "ARTERIOSCLEROSIS-SUSPECT AREA (DEGREE 1)" for the first arteriosclerosis-suspect area 98, and the indication "ARTERIOSCLEROSIS-SUSPECT AREA (DEGREE 2)" for the second arteriosclerosis-suspect area 100, etc.

FIG. 11 shows, as examples of the symbol 104, a circular symbol 104a, a triangular symbol 104b, and a rectangular symbol 104c. Hereinafter, there will be described how to evaluate a degree of arteriosclerosis when each of those symbols 104a, 104b, 104c is displayed. When the circular symbol 104a is displayed, a medical person such as a doctor or a nurse can judge with high reliability that the patient suffers arteriosclerosis, because both the pulse-wave propagation velocity PWV and the augmentation index AI are abnormally high. When the triangular symbol 104b or the rectangular symbol 104c is displayed, the medical person may not be able to judge whether a treatment such as drug administration is needed, in the conventional manner in which only the pulse-wave propagation velocity PWV is used, because the symbol 104b or 104c indicates that the propagation velocity PWV is near the upper-limit value of the normal range of propagation velocity PWV. However, since the triangular symbol 104b indicates that the augmentation index AI is abnormally high, the medical person can judge that a treatment such as drug administration is needed. On the other hand, since the rectangular symbol 104c indicates that the augmentation index AI is normal, the medical person can judge that no treatment is needed at present.

As is apparent from the foregoing description of the illustrated embodiment employing the flow charts of FIGS. 8 and 9, the control device 46 evaluates, at SB6 (the arteriosclerosis evaluating means 82), the degree of arteriosclerosis of the patient based on two sorts of information, i.e., the pulse-wave propagation velocity PWV determined at SB4 (the pulse-wave-propagation-velocity-related-information obtaining means 78) and the augmentation index AI determined at SB5 (the augmentation-related-information obtaining means 80). Therefore, the present apparatus 10 can evaluate the degree of arteriosclerosis with improved accuracy.

In the illustrated embodiment employing the flow charts, the control device 46 operates, at SB7 (the simultaneously displaying means 84), the display device 54 to display, in the two-dimensional coordinate system 102, the symbol 104 at the position having the coordinates corresponding to the pulse-wave propagation velocity PWV determined at SB4 (the pulse-wave-propagation-velocity-related-information obtaining means 78) and the augmentation index AI determined at SB5 (the augmentation-related-information obtaining means 80). Therefore, the medical person can easily make, based on the position of the symbol 104 plotted in the two-dimensional coordinate system 102, a diagnosis about the degree of arteriosclerosis. Since the pulse-wave propagation velocity PWV and the augmentation index AI are used, the accuracy of the diagnosis is improved as compared with the conventional manner in which only the pulse-wave propagation velocity PWV is used. For example, in the case where the medical person cannot easily judge, based on the pulse-wave propagation velocity PWV only, whether a treatment such as drug administration is needed, the person can surely judge that the treatment is needed, if the augmentation index AI indicates arteriosclerosis.

In addition, in the illustrated embodiment employing the flow charts, the display device 54 displays the two-dimensional coordinate system 102 including the respective indications of the arteriosclerosis areas, the arteriosclerosis-suspect areas, and the hypertension area. Therefore, if the symbol 104 is displayed in one of the arteriosclerosis areas, the medical person can judge that the patient suffers arteriosclerosis. In addition, if the symbol 104 is displayed in one of the arteriosclerosis-suspect areas, the medical person can judge that the patient suffers arteriosclerosis and can speculate that the patient's blood pressure is lowered by use of antihypertensive drug. If the symbol 104 is displayed in the hypertension area, the medical person can judge that the patient does not suffer arteriosclerosis but suffers hypertension and can speculate that the patient will suffer arteriosclerosis in future.

Moreover, in the illustrated embodiment employing the flow charts, the control device 46 determines, at SB1 (the incident-wave-peak determining means 74) and SB2 (the reflected-wave-peak determining means 76), the peak pi of the incident-wave component wi, and the peak pr of the reflected-wave component wr, of the carotid pulse wave wc detected by the pressure-pulse-wave sensor 30. In addition, the control device determines, at SB3 and SB4 (the pulse-wave-propagation-velocity-related-information obtaining means 78), the pulse-wave propagation velocity PAW based on the time difference between the peak pi of the incident-wave component wi and the peak pr of the reflected-wave component wr. In addition, the control device 46 determines the augmentation index AI based on the carotid pulse wave wc detected by the pressure-pulse-wave sensor 30. Thus, the present apparatus 10 can measure the pulse-wave-propagation velocity PWV and the augmentation index AI, by using the single, pressure-pulse-wave detecting probe 12.

While the present invention has been described in its preferred embodiment by reference to the drawings, it is to be understood that the invention may otherwise be embodied.

For example, the illustrated arteriosclerosis evaluating apparatus 10 employs both the arteriosclerosis evaluating means 82 and the simultaneously displaying means 84. However, the apparatus 10 may be modified to employ only one of the two means 82, 84.

According to the flow charts shown in FIGS. 8 and 9, the arteriosclerosis evaluating apparatus 10 detects one heartbeat-synchronous pulse of the carotid pulse wave wc and, based on the pulse-wave propagation velocity PWV and the augmentation index AI obtained from the one pulse, the apparatus 10 evaluates the degree of arteriosclerosis and plots the symbol 104. However, the apparatus 10 may be modified to detect, for a prescribed time duration (e.g., 30 seconds), a plurality of heartbeat-synchronous pulse of the carotid pulse wave wc and determine respective averages of respective pulse-wave propagation velocity values PWV and respective augmentation index values AI obtained from those pulses. In the latter case, based on the thus determined averages, the apparatus 10 evaluates the degree of arteriosclerosis and plots the symbol 104.

The arteriosclerosis evaluating apparatus 10 determines the pulse-wave-propagation velocity PWV and the augmentation index AI, based on the pulse wave detected by the single, pressure-pulse-wave detecting probe 12. However, the apparatus may be modified to employ two separate sensors for detecting the pulse-wave-propagation velocity PWV and the augmentation index AI, respectively.

In the arteriosclerosis evaluating apparatus 10, the pressure-pulse-wave detecting probe 12 is worn on the neck 14 of the living subject to detect the carotid pulse wave wc, and the pulse-wave propagation velocity PWV and the augmentation index AI are determined based on the detected, single carotid pulse wave wc. However, the pulse-wave propagation velocity PWV and/or the augmentation index AI may be determined based on a different pulse wave than the carotid pulse wave wc; such as a brachial pulse wave detected from an upper arm of a living subject, a radial pulse wave detected from a wrist of a subject, or a femoral pulse wave detected from a femur of a subject. Alternatively, the apparatus 10 may be modified to employ two heartbeat-synchronous-signal detecting devices which are adapted to be worn on two different body portions of a living subject, and determine a pulse-wave propagation velocity PWV based on two heartbeat-synchronous signals detected by the two heartbeat-synchronous-signal detecting devices.

In the arteriosclerosis evaluating apparatus 10, the arteriosclerosis-evaluate map 86 defines the higher than 900 cm/s range of the pulse-wave propagation velocity PWV as the abnormal range thereof, and defines the higher than 10% range of the augmentation index AI as the abnormal range thereof. The abnormal ranges are not limited to those specific ranges. For example, those abnormal ranges may be changed depending upon individual differences of patients. In addition, the arteriosclerosis areas displayed in the two-dimensional coordinate system 102 are not limited to the specific areas employed in the illustrated embodiment, and may be changed, as needed, depending upon individual differences of patients. In the case where pulse-wave propagation velocity PWV is measured at a different portion of a living subject, the arteriosclerosis-evaluate map 86 is modified to define a different abnormal range of the pulse-wave propagation velocity PWV. For example, when propagation velocity PWV is measured at a body portion between an upper arm and an ankle of a living subject, the map 86 may be modified to define, e.g., a higher than 1,400 cm/s range of the propagation velocity PWV as an abnormal range thereof.

The present invention may be embodied with other changes without departing from the spirit of the invention.

What is claimed is:

1. An apparatus for evaluating a degree of arteriosclerosis of a living subject, comprising:
   a pulse-wave-propagation-velocity-related-information obtaining device which obtains pulse-wave-propagation-velocity-related information that is related to a velocity at which a pulse wave propagates in the subject;
   a pulse-wave sensor which is adapted to be worn on a body portion of the subject and detects the pulse wave from the body portion;
   an augmentation-related-information obtaining means for obtaining augmentation-related information that is related to an augmentation of an amplitude of the pulse wave detected by the pulse-wave sensor from an amplitude of an incident-wave component which is contained in the pulse wave; and
   an arteriosclerosis evaluating means for evaluating the degree of arteriosclerosis of the subject, based on the pulse-wave-propagation-velocity-related information obtained by the pulse-wave-propagation-velocity-related-information obtaining device and the augmentation-related information obtained by the augmentation-related-information obtaining means, according to a prescribed relationship between (A) (a1) pulse-wave-propagation-velocity-related information and (a2) augmentation-elated information and (B) degree of arteriosclerosis.

2. An apparatus according to claim 1, wherein the pulse-wave-propagation-velocity-related-information obtaining device comprises:
   an incident-wave-peak determining means for determining a peak of the incident-wave component contained in the pulse wave detected by the pulse-wave sensor;
   a reflected-wave-peak determining means for determining a peak of a reflected-wave component which is contained in the pulse wave detected by the pulse-wave sensor; and
   an obtaining means for obtaining the pulse-wave-propagation-velocity-related information based on the peak of the incident-wave component determined by the incident-wave-peak determining means and the peak of the reflected-wave component determined by the reflected-wave-peak determining means.

3. An apparatus according to claim 2, wherein the incident-wave-peak determining means determines the peak of the incident-wave component, by differentiating the pulse wave detected by the pulse-wave sensor.

4. An apparatus according to claim 3 wherein the incident-wave-peak determining means comprises:
   means for determining a rising point and a maximal point of a heartbeat-synchronous pulse of the pulse wave detected by the pulse-wave sensor;
   means for differentiating a portion of the pulse wave between the rising point and the maximal point; and
   means for determining, as the peak of the incident-wave component, an inflection point of the differentiated portion of the pulse wave.

5. An apparatus according to claim 2, wherein the reflected-wave-peak determining means comprises:
   means for differentiating the pulse wave detected by the pulse-wave sensor; and
   means for determining, as the peak of the reflected-wave component, a maximal point of the pulse wave.

6. An apparatus according to claim 1, wherein the pulse-wave sensor comprises a pressure-pulse-wave sensor which is adapted to be pressed against an artery of the subject and detects, as the pulse wave, a pressure pulse wave produced from the artery.

7. An apparatus according to claim 6, wherein the pressure-pulse-wave sensor detects the pressure pulse wave produced from the artery selected from the group consisting of a carotid artery, a brachial artery, a radial artery, and a femoral artery.

8. An apparatus according to claim 6, wherein the pressure-pulse-wave sensor comprises a plurality of pressure-sensing elements each of which can detect the pressure pulse wave produced from the artery, and a press surface in which the pressure-sensing elements are arranged in at least one array such that in a state in which the pressure-pulse-wave sensor is worn on the body portion and the press surface is pressed against a surface of the body portion, the array of the pressure-sensing elements crosses over the artery and at least one of the pressure-sensing elements is positioned right above the artery.

9. An apparatus for evaluation of a degree of arteriosclerosis of a living subject, comprising:

a pulse-wave-propagation-velocity-related-information obtaining device which obtains pulse-wave-propagation-velocity-related information that is related to a velocity at which a pulse wave propagates in the subject;

a pulse-wave sensor which is adapted to be worn on a body portion of the subject and detects the pulse wave from the body portion;

an augmentation-related-information obtaining means for obtaining augmentation-related information that is related to an augmentation of an amplitude of the pulse wave detected by the pulse-wave sensor from an amplitude of an incident-wave component which is contained in the pulse wave; and a simultaneously displaying device which simultaneously displays the pulse-wave-propagation-velocity-related information obtained by the pulse-wave-propagation-velocity-related-information obtaining device and the augmentation-related information obtained by the augmentation-related-information obtaining means.

10. An apparatus according to claim 9, wherein the augmentation-related-information obtaining device comprises augmentation-index determining means for determining, as the augmentation-related information, an augmentation index indicative of the augmentation of the amplitude of the pulse wave from the amplitude of the incident-wave component, and wherein the simultaneously displaying device comprises a display device which displays, in a two-dimensional coordinate system defined by a first axis representative of pulse-wave-propagation-velocity-related information and a second axis representative of augmentation index, a symbol at a position having a pair of coordinates corresponding to the pulse-wave-propagation-velocity-related information obtained by the pulse-wave-propagation-velocity-related-information obtaining device and the augmentation index determined by the augmentation-index determining means.

11. An apparatus according to claim 10, wherein the display device displays the two-dimensional coordinate system which includes (A) an arteriosclerosis area corresponding to an arteriosclerosis range of each of the pulse-wave-propagation-velocity-related information and the augmentation index represented by the first and second axes, and (B) al least one of (b1) an arteriosclerosis-suspect area corresponding to a normal range of the pulse-wave-propagation-velocity-related information and the arteriosclerosis range of the augmentation index and (b2) a hypertension area corresponding to the arteriosclerosis range of the pulse-wave-propagation-velocity-related information and a normal range of the augmentation index.

12. An apparatus according to claim 9, wherein the pulse-wave-propagation-velocity-related-information obtaining device comprises:

an incident-wave-peak determining means for determining a peak of the incident-wave component contained in the pulse wave detected by the pulse-wave-sensor;

a reflected-wave-peak determining means for determining a peak of a reflected-wave component which is contained in the pulse wave detected by the pulse-wave sensor; and an obtaining means for obtaining the pulse-wave-propagation-velocity-related information based on the peak of the incident-wave component determined by the incident-wave-peak determining means and the peak of the reflected-wave component determined by the reflected-wave-peak determining means.

13. An apparatus according to claim 9, further comprising an arteriosclerosis evaluating means for evaluating the degree of arteriosclerosis of the subject, based on the pulse-wave-propagation-velocity-related information obtained by the pulse-wave-propagation-velocity-related-information obtaining device and the augmentation-related information obtained by the augmentation-related-information obtaining means, according to a prescribed relationship between (A) (a1) pulse-wave-propagation-velocity-related information and (a2) augmentation-elated information and (B) degree of arteriosclerosis.

* * * * *